United States Patent [19]

Rubin

[11] Patent Number: 5,158,978

[45] Date of Patent: Oct. 27, 1992

[54] THYROID HORMONE TREATMENT OF ACUTE CARDIOVASCULAR COMPROMISE

[75] Inventor: Leo Rubin, Suffern, N.Y.

[73] Assignee: British Technology Group (U.S.A.), Gulph Mills, Pa.

[21] Appl. No.: 723,716

[22] Filed: Jun. 18, 1991

Related U.S. Application Data

[63] Continuation of Ser. No. 495,354, Mar. 19, 1990, abandoned, which is a continuation-in-part of Ser. No. 475,360, Feb. 5, 1990, abandoned.

[51] Int. Cl.⁵ .......................................... A61K 31/195
[52] U.S. Cl. .................................. 514/567; 514/821; 514/921
[58] Field of Search ........................ 514/567, 821, 921

[56] References Cited

U.S. PATENT DOCUMENTS

| | | | |
|---|---|---|---|
| 2,803,654 | 8/1957 | Anthony et al. | 562/447 |
| 3,109,024 | 10/1963 | Meltzer et al. | 562/447 |
| 4,470,962 | 9/1984 | Keith et al. | 424/449 |
| 4,666,441 | 5/1987 | Andriola et al. | 424/448 |
| 4,818,540 | 4/1989 | Chien et al. | 424/448 |
| 4,863,970 | 9/1989 | Patel et al. | 514/784 |

FOREIGN PATENT DOCUMENTS

| | | |
|---|---|---|
| 2354101 | 6/1978 | France . |
| 63-79824 | 4/1988 | Japan . |
| WO8907454 | 8/1989 | PCT Int'l Appl. . |

OTHER PUBLICATIONS

Gay, R. et al. Effects of L-Thyroxine in Rats with Chronic Heart Failure After Myocardial Infarction *Am. J. Physiol.* 253:H341-6 (1987).
Kranz, D. et al., The influence of hyperthyroidism & hypothyroidism on the wound healing of experimental myocardial infection in the rat *Exp. Path. Bd.* 12: 129-136 (1976).
Siverberg et al., Cardiology Series 5(2):6-26 (1982).
Novitsky et al., "Triiodothyronine Therapy in the Cardiac Transplant Recipient", Trans. Proc., 20:65-68 (1988).
Novitsky et al., "Ionotropic Effect of Triiodothyronine (T₃) in Low Cardiac Output Following Cardioplegic Arrest and Cardiopulmonary Bypass: an Initial Experience in Patients Undergoing Open Heart Surgery", Eur. J. Cardiothorac. Surg., 3:140-145 (1989).
Novitsky et al., "Improved Cardiac Allograft Function Following Triiodothyronine Therapy to Both Donor and Recipient", Transplantation, 49:311-316 (1990).
Novitsky et al., "Triiodothyronine as an Inotropic Agent After Open Heart Surgery", J. Thorac. Cardiovasc. Surg., 98:972-978 (1989).
Novitsky et al., "Effect of Triiodothyronine (T₃) on Myocardial High Energy Phosphates and Lactate After Ischemia and Cardiopulmonary Bypass", J. Thorac. Cardiovasc. Surg., 96:600-607 (1988).
Koga et al., "Primary Hypothyroidism in Severe Chronic Heart Failure", Jpn. J. Med., 27:42-48 (1988).
Meyer et al., "Treatment of Dopamine-Dependent Shock With Triiodothyronine: Preliminary Results", Deutsch Med. Wochenschr., 104:1711-1714 (1979). (Medline Abstact from the German article and the German article: Behandlung des dopaminab hangigen Schocks mit Tijodthyronin).
Meyer et al., "Treatment of Dopamine Dependent Schock With Triiodothyronine-Preliminary Report", Intensivmedizin, 17:148-152 (1980) (Medline Abstract from the German article and the German article: Behandlung des dopaminabhangigen Schocks mit Trijodthyronin—ein Vorlaufiger Bericht).
Hesch et al., "Treatment of Dopamine-Dependent Schock with Triiodothyronine", Endocr. Res. Commun., 8:229-237 (1981).
Moley et al., "Hypothyroidism Abolishes the Hyperdynamic Phase and Increases Susceptibility to Sepsis", J. Surg. Res., 36:265-273 (1984).
Novitsky et al., "Inotropic Effect of Triiodothyronine Following Myocardial Ischemia and Cardiopulmonary Bypass: An Experimental Study in Pigs", Ann. Thorac. Surg., 45:50-55 (1988).
British National Formulary No. 16 (1988) pp. 111-112.
Hylander et al., "Long-Term ECG Recording in Thyroxine-Substituted Hyopothyroid Subjects", Acta. Med. Scand., 222:429-432 (1987).
Paschen et al., "Alteration in Thyroid Hormone Concentration During and After Coronary Bypass Operation", Ann. Endocrinol., 44:239-242 (1983).
Xiang et al., "Effect of Myo-Inositol and T₃ on Myocardial Lipids and Cardiac Function in Streptozocin³Induced Diabetic Rats", Diabetes, 37:1542-1548 (1988).
Goodkind et al., "Effect of Thyroxine on Ventricular Myocardial Contractility and ATPase Activity in Guinea Pigs", Amer. J. Phys., 226:66-72 (1974).
Novitzky et al., "The Value of Triiodothyronine (T₃) in the Rescue of a Failing Heart following Valve Replacement", The 23rd Annual Meeting of the Society of Thoracic Surgeons, Sep. 21-23, 1987 in Toronto, Ontario, Canada.
Hylander et al., "The Cardiovascular Response at Rest and During Exercise in Hypothyroid Subjects to Thyroxine Substitution", Clin. Cardiol., 6:116-124 (1983).
Labhart, "Clinical Endocrinology" Springer Verlag (1976) pp. 146-147.
Buccino et al., "Influence of the Thyroid State on the Intrinsic Contractile Properties and the Energy Stores of the Myocardium", J. Clin. Invest., 46:1669 (1967).

(List continued on next page.)

*Primary Examiner*—Richard L. Raymond
*Assistant Examiner*—Gary E. Hollinden
*Attorney, Agent, or Firm*—Brumbaugh, Graves, Donohue & Raymond

[57] ABSTRACT

A method for the treatment of patients with acute cardiovascular compromise by administering a therapeutically effective amount of thyroid hormones. Methods of administration are included.

69 Claims, No Drawings

OTHER PUBLICATIONS

Wortsman et al., "Hypothyroxinemia in Cardiac Arrest", Arch. Intern. Med., 147:245–248 (1987).

Haynes et al., "Thyroid And Antithyroid Drugs" in: The Pharmacological Basis of Therapeutics, Gilman et al., eds., Macmillan Pub. Co. (1985).

Physicians Desk Reference Barnhart Publ., N.J. pp. 1558, 1801 and 962 (1990).

Bacci et al., "Cardiac Arrest After Intravenous Administration of Levothyroxine", J.A.M.A., 245:920 (1981).

Bergeron et al., "Myocardial Infarction, Severe Reversible Ischemia, and Shock Following Excess Thyroid Administration in a Woman With Normal Coronary Arteries", Arch. Intern. Med., 148:1450–1453 (1988).

Morkin et al., "Biochemical and Physiologic Effects of Thyroid Hormone on Cardiac Performance", Prog. Card. Dis., 25:435–464 (1983).

THYROID HORMONE TREATMENT OF ACUTE CARDIOVASCULAR COMPROMISE

This application is a continuation of application Ser. No. 07/495,354, filed on Mar 19, 1990, now abandoned, which is a continuation-in-part of our application Ser. No. 07/475,360, filed Feb. 5, 1990, now abandoned.

BACKGROUND OF THE INVENTION

This invention relates to the use of thyroid hormones and related compounds, to facilitate cardiac resuscitation and enhance cardiac function.

CARDIAC ARREST

Cardiac arrest occurs when there is electrical and mechanical dysfunction in the heart. The survival of cardiac arrest depends on timely defibrillation and administration of proper medications. A more effective treatment is critical since annual morbidity from cardiac arrest exceeds 540,000 and despite our current armamentarium there is less than a 25% survival rate.

THYROXINE REPLACEMENT THERAPY

Thyroid hormones include the L-forms of thyroxine (0-(4-Hydroxy-3,5-diiodophenyl)-3,5-diidotyrosine; T4; hereinafter thyroxine) and 3, 5, 3' triiodothyronine (hereinafter triiodothyranine or T3). T3 is qualitatively similar to thyroxine in its biological effect but is more potent on a molar basis. Although some T3 is synthesized in the thyroid gland, the majority of naturally occurring T3 is synthesized by metabolism of thyroxine in peripheral tissues by the enzyme 5' deiodinase.

Thyroxine is the sole thyroid hormone in clinical use today. This is largely due to its availability and relatively long half-life of 6-7 days. Thyroxine binds avidly to thyroxine-binding globulin in human serum and is thus protected from metabolism and excretion. Pure T3 is not in clinical use due to its relative unavailability and less than avid binding to thyroxine-binding globulin resulting in a half-life of two days or less.

Thyroid hormones are obtained from natural sources, such as bovine thyroid glands or synthesized in vitro by methods such as that described by Anthony et al., in U.S. Pat. No. 2,803,654 issued Aug. 20, 1957. Analogs of thyroxine may also function to relieve hypothyroidism. A series of thyroxine analogs and methods of synthesis are described by Meltzer et al., in U.S. Pat. No. 3,109,024 issued Oct. 29, 1963.

Thyroxine is routinely used in treatment of patients lacking adequate thyroid function. Such patients are those with hypothyroidism, (myxedema), goiter or cretinism. In the case of hypothyroidism the addition of thyroxine can effectively restore the normal euthyroid state, however, some effects of cretinism may be irreversible if thyroid hormone replacement is not begun immediately after birth.

Thyroxine has been shown to play a negative role in heart function. Hyperthyroidism, caused by excess thyroid hormone, exhibits a number of cardiac dysfunctions such as heart palpitations, dyspnea, tachycardia, systolic hypertension and a variety of heart murmurs. The effects of hyperthyroidism on the heart may also include premature beats, auricular fibrillation, increased stroke volume, increased cardiac output and although the peripheral vascular resistance decreases, the myocardial workload becomes greater. Labhart, "Clinical Endocrinology", Springer Verlag (1976). Hyperthyroidism may lead to angina, arrhythmias, and heart failure. In hyperthyroid cats papillary muscles were shown to have a greater force-velocity relationship than euthyroid and hypothyroid cats. Buccino et al., "Influence of the Thyroid State on the Intrinsic Contractile Properties and the Energy Stores of the Myocardium", J. Clin. Invest., 46:1669 (1967).

Thyroxine increases the heart rate and force of the beats thus increasing cardiac output. Thyroxine is found to be depleted in some critically ill patients which have had a heart attack theorized to be in response to the stress of the heart attack. Wortsman et al., "Hypothyroxinemia in Cardiac Arrest", Arch Intern. Med., 147:245-248 (1987). The effect of thyroxine on the heart has been hypothesized to be the result of a change in the isozyme pattern of myosin. Haynes et al., "Thyroid and Antithyroid Drugs", in: The Pharmacological Basis of Therapeutics, Gilman et al., eds, Macmillan Pub. Co. (1985). Such an effect would require changes in the expression or stability of messenger RNA encoding the myosin isozymes and thus would not be immediate but would require prolonged exposure to excess amount of thyroxine.

Hypothyroidism, distinguished by a lack of sufficient thyroxine, is characterized by hemodynamic alterations that include reduced stroke volume, heart rate and cardiac output and increased peripheral vascular resistance; although these abnormalities are normalized by long-term thyroxine replacement, other cardiac problems may be exacerbated by thyroxine replacement. The restoration of the euthyroid state may exacerbate ischemic heart disease; elderly patients with coronary artery disease are given only small doses of thyroxine which are gradually increased so as to avoid heart failure. Thyroxine therapy of hypothyroid patients leads to increased arrhythmias due to atrial premature beats and increased heart rate.

Due to its effect on the heart, administration of thyroxine is contraindicated for patients with heart conditions such as tachyarrhythmias, acute myocardial infarction, cardiac instability and severe heart disease. See for instance Physicians' Desk Reference, Barnhart, Pub., N.J. pp. 1558, 1801 and 962. Thyroxine can have serious cardiac effects even when given to patients without underlying heart disease. For instance, a sudden, large load of thyroxine may have a direct and rapid effect on the myocardium, causing cardiac arrest. Bacci et al., "Cardiac Arrest After Intravenous Administration of Levothyroxine", J.A.M.A., 245:920 (1981). Thyroxine therapy for hypothyroidism caused severe segmental left ventricular ischemic changes, subendocardial infarction, and cardiogenic shock in a patient with normal coronary anatomy. Bergeron et al., "Myocardial Infarction, Severe Reversible Ischemia, and Shock Following Excess Thyroid Administration in a Woman With Normal Coronary Arteries", Arch. Intern. Med., 148:1450-1453 (1988).

Hypothyroid patients normally respond to oral administration of 25 to 200 μg of thyroxine, provided in pills. However, in cases where oral administration of thyroxine is not possible or in an emergency such as where hypothyroidism has led to coma, thyroxine is administered parenterally either intravenously or by intramuscular injection. Parenteral administration is at the concentration normally taken orally except in the case of emergency where up to 200–500 μg may be administered intravenously. Thyroxine for parenteral administration is provided lyophilized to be reconstituted with saline solution immediately prior to use.

Notwithstanding the history of the ability of thyroxine to cause heart attacks in patients with both underlying heart disease and normal coronary anatomy, it has now been found that an infusion of thyroid hormones, their analogues or derivatives effects cardiac resuscitation in patients undergoing cardiac arrest. The effect of thyroid hormones is almost immediate and occurs even where standard treatments have failed. Thyroid hormones have been found to effect both the chronotropic and ionotropic heart functions. It has also been found that thyroid hormones are therapeutically effective in other cardiac indications such as cardiomyopathies and bradyarrhythmias.

SUMMARY OF THE INVENTION

Infusion of thyroid hormones has now been found to be effective in the treatment of patients with cardiovascular compromise.

DETAILED DESCRIPTION OF THE INVENTION

It has now been found that infusion of thyroid hormones such as thyroxine, T3, their analogues, derivatives and combinations thereof (hereinafter thyroid hormones) effectively resuscitates patients undergoing cardiac arrest. Thyroid hormones administered to patients with cardiovascular compromise are effective to restore or improve cardiac rhythm and function. Thyroid hormones are effective where standard treatments fail and are thus an improvement over standard treatment methods.

Thyroid hormone therapy for cardiovascular compromise includes but is not limited to adjunct therapy in any mechanical cardiac support system, electromechanical dissociation (EMD), post-cardiopulmonary bypass, cardiac arrest, cardiomyopathies and bradyarrhythmias. Adjunct therapy in any mechanical cardiac support system is useful to enhance function of the heart during and after support in situations including but not limited to cardiopulmonary bypass, ventricular assist device and intraaortic balloon. Thyroid hormone treatment is indicated in EMD which is a result of post defibrillation and myocardial infarction and occurs when the electrical and physical actions of the heart become dissociated such that the electrical stimulation no longer produces a concomitant physical movement. Thyroid hormone treatment is useful in post-cardiopulmonary bypass when the attempt is made to restart the heart with epicardial defibrillation or when initial attempts are unsuccessful at restoring effective heart contraction. Cardiomyopathies are the result of ischemic, metabolic or idiopathic disorders or are the result of microbial infections such as those caused by viral, bacterial, fungal or parasitic infection. Bradyarrhythmias are caused by cardiovascular disease or arise post cardiac arrest.

For cardiac resuscitation thyroid hormone is administered either directly into the heart cavity, parenterally or directly to the pulmonary system.

Direct administration into the heart includes but is not limited to direct intracardiac injection. Parenteral administration includes but is not limited to injection into a central venous line infusion via a pump or direct intravenous injection. Pulmonary administration includes but is not limited to direct endotracheal injection such as through an endotracheal tube or through an airway system such as through a vaporizer, atomizer or an endotracheal tube.

In administration of thyroid hormones to patients with cardiomyopathies or bradyarrhythmias, methods of administration include but are not limited to parenteral, pulmonary, topical or gastrointestinal. Parenteral and pulmonary administrations are such as described above. Compositions for topical application include but are not limited to creams, ointments, gels, rinses and transdermal patches. Such compositions are known in the art, any liquid physiologically acceptable base in which thyroid hormones are at least minimally dissolved is suitable for topical use in the present invention. Transdermal patches are described for instance in U.S. Pat. No. 4,818,540 issued Apr. 4, 1989 to Chien et al.

The preferred thyroid hormone dosage ranges depend on the specific activity of the thyroid hormone used. For instance, in the case of thyroxine, the dosage can be from approximately 100 μg to about 10 g when given parenterally in at least one rapid bolus injection with repeated injections of comparable amounts as necessary to attain and sustain hemodynamic stability. In the case of T3, the preferred dosage ranges from approximately 1 μg to about 1 mg when given parenterally in at least one rapid bolus injection with repeated injections of comparable amounts as necessary to attain and sustain hemodynamic stability. The amount of thyroid hormones used depends on the weight of the patient, the severity of the situation, the underlying pathology and time from onset of arrest with greater amounts being given to heavier patients and increasing time from cardiac arrest. It is preferred that patients undergoing cardiac resuscitation receive thyroid hormones in conjunction with defibrillation although thyroid hormones may be administered in the absence of other therapy.

Patients who have not arrested such as those with cardiomyopathies and bradyarrhythmias may require smaller doses in the range of approximately 100 μg to 500 μg thyroxine per day or approximately 1 μg to about 50 μg T3 per day preferably by gastrointestinal or topical administration.

Overdoses of thyroid hormones can be immediately aborted with intravenous doses of β-blockers including but not limited to propanolol and metoprolol. Also, if thyroxine is used in large doses, treatment with β-blockers may follow to prevent the effects of hyperthyroidism on the heart. If T3 is used, β-blockers may not be necessary as T3 is rapidly metabolized and/or excreted from the body. T3 is thus preferred over thyroxine as it is more active on a molar basis and gives rise to fewer hyperthyroid symptoms.

The invention also includes packaged combinations for parenteral administration of thyroid hormones to patients with cardiovascular compromise. Such packaged combinations include a device suitable for injection, thyroxine, T3, analogues, derivatives thereof alone or in combination either dissolved in a physiologically acceptable diluent or powdered in combination with a physiologically acceptable diluent for dilution just prior to use. The diluent can be formulated to additionally contain various therapeutically effective substances which enhance the heart functions including but not limited to calcium and magnesium in therapeutically acceptable amounts.

The invention further includes atomizers and vaporizers containing a therapeutically effective concentration of thyroid hormones for pulmonary infusion. The invention further includes compositions for topical application including but not limited to ointments, creams, rinses, gels and transdermal patches containing therapeutically effective amounts of thyroid hormone suitable for treatment of cardiomyopathies and bradyarrhythmias.

The methods of formulating suitable devices for injection, compositions for topical application, atomizers and vaporizers are known in the art and will not be described in detail. An example of a suitable injection device is the Abboject, "Unit of Use Syringe" (Abbott Laboratory) which delivers a single dose of adrenalin to the heart via an intracardiac needle.

It is apparent from the following examples that thyroxine effects cardiac resuscitation when other standard treatments have failed. Thyroxine restored normal cardiac function where standard methods had failed and did not cause any symptoms of hyperthyroidism in the treated dogs. However, since dogs lack thyroxine-binding globulin, thyroxine is rapidly metabolized or excreted after administration. In humans, thyroxine persists up to a week after treatment thus its effects are counteracted by $\beta$-blockers administered subsequent to thyroxine treatment. T3, which does not bind avidly to thyroxine-binding globulin is therefore the preferred thyroid hormone for use in humans despite the fact that T3 has heretofore not been used clinically. T3 is preferred to thyroxine as it has higher specific activity than thyroxine and does not persist after administration therefore decreasing or eliminating the need for subsequent $\beta$-blocker therapy. The effect of T3 in humans thus directly correlates with the effect of thyroxine in dogs.

The following examples are meant to describe but not limit the present invention.

EXAMPLE 1

Using a Ventritex bedside, external pulse generator and defibrillator, rapid pacing at a rate of 30-50 milliseconds for approximately 4-6 seconds was used to induce ventricular fibrillation in a mongrel dog weighing 30-50 pounds.

Defibrillation threshold in the dog was established by repeated attempts at fibrillation and defibrillation via the Ventritex pulse generator according to the manufacturer's instructions. During one episode, while attempting to determine threshold defibrillation with standard shock (250 volts (V)) and "rescue shock" (950 V) were ineffective. Large energy pulses were then applied via an external defibrillator (Hewlett Packard), resulting in cardiac standstill as determined by electrocardiographic monitoring. The dog was then paced with 10 V of 1 millisecond duration at a rate of 100 beats per minute (bpm).

Every attempt at turning off the pacing unit resulted in returning the rhythm to standstill as evidenced by ECG and lack of palpable pulse. After approximately three minutes of cardiac standstill without any effective rhythm, the dog was given an intravenous bolus of 250 $\mu$g of thyroxine. The thyroxine was obtained from Stris Laboratories Inc., Ariz. and prepared according to the manufacturer's instructions. Approximately 1-1.5 minutes after receiving thyroxine the dog reverted to normal cardiac rhythm with a good palpable pulse.

EXAMPLE 2

After establishing defibrillation threshold as described in Example 1, external defibrillation was administered eight times as in Example 1, without establishing normal cardiac rhythm. The dog was then given an intravenous bolus injection of 250 $\mu$g thyroxine. Approximately 1 minute after receiving the thyroxine the dog developed a spontaneous rhythm alternating between sinus and supraventricular. The dog subsequently developed A-V dissociation, and was given a second intravenous bolus injection of 250 $\mu$g thyroxine upon which the dog reverted to normal cardiac rhythm with an effective pulse. The dog maintained a sinus rhythm and good pulse until it was sacrificed.

EXAMPLE 3

A dog was put into fibrillation and the defibrillation threshold was obtained as described in Example 1. Throughout the experiment the dog was on a ventilator to maintain oxygenation. Defibrillation was attempted at 250 V without effect. A rescue shock of 950 V was then applied as in Example 1 without effect. The 950 V shock was repeated 23 times without effect. At this point the dog's chest was opened and a shock was applied directly to the heart with internal epicardial paddles at 400 joules using a Hewlett Packard defibrillator as per the manufacturer's instructions.

After the direct cardiac stimulation the dog briefly came out of fibrillation but immediately returned to ventricular fibrillation with no apparent mechanical activity. The heart was again stimulated with internal epicardial paddles at 400 joules and the dog reverted to a tachyarrhythmia with electromechanical dissociation which then degenerated to ventricular fibrillation. The dog was then shocked with 950 V externally and defibrillation persisted. At this point, about 8.5 minutes after initial onset of fibrillation, thyroxine was administered in a bolus of 250 $\mu$g intracardiac. After approximately 100 seconds and four defibrillation attempts the dog developed atrioventricular dissociation and subsequently reverted to a super a ventricular tachyardia with electromechanical dissociation. A second intravenous bolus of thyroxine 250 $\mu$g was then administered and in less than 20 seconds the dog developed an effective pulse and rapidly reverted back to a sinus rhythm. The following morning the dog was alert and ate well.

I claim:

1. A method for emergency treatment of a patient with spontaneous cardiac arrest for restoring effective cardiac function, comprising administering to the patient a therapeutically effective amount of a thyroid hormone selected from the group consisting of thyroxine, triiodothyronine and agonists thereof.

2. A method according to claim 1, wherein the amount of thyroid hormone administered to the patient is effective for restoring cardiac function.

3. A method according to claim 1, wherein the thyroid hormone is administered by direct injection into a heart cavity of the patient.

4. A method according to claim 1, wherein the thyroid hormone is administered by parenteral injection.

5. A method according to claim 4, wherein the thyroid hormone is administered by parenteral intravenous injection.

6. A method according to claim 4, wherein the thyroid hormone is administered by direct parenteral injection into a central venous line of the patient.

7. A method according to claim 1, wherein the thyroid hormone is administered directly to the pulmonary system of the patient.

8. A method according to claim 7, wherein the thyroid hormone is administered directly to the pulmonary system by direct endotracheal injection.

9. A method according to claim 7, wherein the thyroid hormone is administered directly to the pulmonary system by infusion through a respiratory airway of the patient.

10. A method according to claim 1, 3, or 6, wherein the thyroid hormone is administered in at least one rapid bolus injection.

11. A method according to claim 1, wherein the thyroid hormone is thyroxine.

12. A method according to claim 11, wherein the therapeutically effective amount of thyroxine is in the range of 500 µg to 10 g.

13. A method according to claim 1, wherein the thyroid hormone is triiodothyronine.

14. A method according to claim 13, wherein the therapeutically effective amount of triiodothyronine is in the range of 50 µg to 1 mg.

15. A method for emergency treatment of a patient with spontaneous cardiac arrest resulting from electromechanical dissociation comprising administering to the patient a thyroid hormone selected from the group consisting of thyroxine, triiodothyronine and agonists thereof in an amount effective to establish cardiac function.

16. A method according to claim 15, wherein the thyroid hormone is administered by direct injection into a heart cavity of the patient.

17. A method according to claim 15, wherein the thyroid hormone is administered by parenteral injection.

18. A method according to claim 17, wherein the thyroid hormone is administered by parenteral intravenous injection.

19. A method according to claim 17, wherein the thyroid hormone is administered by direct parenteral injection into a central venous line of the patient.

20. A method according to claim 15, wherein the thyroid hormone is administered directly to the pulmonary system of the patient.

21. A method according to claim 20, wherein the thyroid hormone is administered directly to the pulmonary system by direct endotracheal injection.

22. A method according to claim 20, wherein the thyroid hormone is administered directly to the pulmonary system by infusion through a respiratory airway of the patient.

23. A method according to claim 15, 16, or 19, wherein the thyroid hormone is administered in at least one rapid bolus injection.

24. A method according to claim 15, wherein the thyroid hormone is thyroxine.

25. A method according to claim 24, wherein the therapeutically effective amount of thyroxine is in the range of 500 µg to 10 g.

26. A method according to claim 15, wherein the thyroid hormone is triiodothyronine.

27. A method according to claim 26, wherein the therapeutically effective amount of triiodothyronine is in the range of 50 µg to 1 mg.

28. A method for emergency treatment to restore effective cardiac function in a patient with spontaneous cardiac electrical standstill, comprising administering to the patient a thyroid hormone selected from the group consisting of thyroxine, triiodothyronine and agonists thereof in an amount effective to establish a cardiac rhythm.

29. A method according to claim 28, wherein the cardiac rhythm is a normal sinus rhythm.

30. A method according to claim 28, wherein the thyroid hormone is administered by direct injection into a heart cavity of the patient.

31. A method according to claim 28, wherein the thyroid hormone is administered by parenteral injection.

32. A method according to claim 31, wherein the thyroid hormone is administered by parenteral intravenous injection.

33. A method according to claim 31, wherein the thyroid hormone is administered by direct parenteral injection into a central venous line of the patient.

34. A method according to claim 28, wherein the thyroid hormone is administered directly to the pulmonary system of the patient.

35. A method according to claim 34, wherein the thyroid hormone is administered directly to the pulmonary system by direct endotracheal injection.

36. A method according to claim 34, wherein the thyroid hormone is administered directly to the pulmonary system by infusion through a respiratory airway of the patient.

37. A method according to claim 28, 30, or 33, wherein the thyroid hormone is administered in at least one rapid bolus injection.

38. A method according to claim 28, wherein the thyroid hormone is thyroxine.

39. A method according to claim 38, wherein the therapeutically effective amount of thyroxine is in the range of 500 µg to 10 g.

40. A method according to claim 28, wherein the thyroid hormone is triiodothyronine.

41. A method according to claim 40, wherein the therapeutically effective amount of triiodothyronine is in the range of 50 µg to 1 mg.

42. A method for emergency treatment to restore effective cardiac function in a patient with spontaneous cardiac electrical standstill caused by a disease, comprising administering to the patient a thyroid hormone selected from the group consisting of thyroxine, triiodothyronine and agonists thereof in an amount effective to establish a cardiac rhythm.

43. A method according to claim 42, wherein the cardiac rhythm is a normal sinus rhythm.

44. A method according to claim 42, wherein the thyroid hormone is administered by direct injection into a heart cavity of the patient.

45. A method according to claim 42, wherein the thyroid hormone is administered by parenteral injection.

46. A method according to claim 45, wherein the thyroid hormone is administered by parenteral intravenous injection.

47. A method according to claim 45, wherein the thyroid hormone is administered by direct parenteral injection into a central venous line of the patient.

48. A method according to claim 42, wherein the thyroid hormone is administered directly to the pulmonary system of the patient.

49. A method according to claim 48, wherein the thyroid hormone is administered directly to the pulmonary system by direct endotracheal injection.

50. A method according to claim 48, wherein the thyroid hormone is administered directly to the pulmonary system by infusion through a respiratory airway of the patient.

51. A method according to claim 42, 44, or 47, wherein the thyroid hormone is administered in at least one rapid bolus injection.

52. A method according to claim 42, wherein the thyroid hormone is thyroxine.

53. A method according to claim 42, wherein the therapeutically effective amount of thyroxine is in the range of 500 μg to 10 g.

54. A method according to claim 42, wherein the thyroid hormone is triiodothyronine.

55. A method according to claim 54, wherein the therapeutically effective amount of triiodothyronine is in the range of 50 μg to 1 mg.

56. A method for establishing effective cardiac function in a heart of a patient in spontaneous cardiac arrest in which defibrillation is applied and does not establish a cardiac rhythm in the patient, comprising administering to the patient a thyroid hormone selected from the group consisting of thyroxine, triiodothyronine and agonists thereof in an amount effective to establish a cardiac rhythm.

57. A method according to claim 56, wherein the cardiac rhythm is a normal sinus rhythm.

58. A method according to claim 56, wherein the thyroid hormone is administered by direct injection into a heart cavity of the patient.

59. A method according to claim 56, wherein the thyroid hormone is administered by parenteral injection.

60. A method according to claim 59, wherein the thyroid hormone is administered by parenteral intravenous injection.

61. A method according to claim 59, wherein the thyroid hormone is administered by direct parenteral injection into a central venous line of the patient.

62. A method according to claim 56, wherein the thyroid hormone is administered directly to the pulmonary system of the patient.

63. A method according to claim 62, wherein the thyroid hormone is administered directly to the pulmonary system by direct endotracheal injection.

64. A method according to claim 62, wherein the thyroid hormone is administered directly to the pulmonary system by infusion through a respiratory airway of the patient.

65. A method according to claim 56, 58, or 61, wherein the thyroid hormone is administered in at least one rapid bolus injection.

66. A method according to claim 56, wherein the thyroid hormone is thyroxine.

67. A method according to claim 66, wherein the therapeutically effective amount of thyroxine is in the range of 500 μg to 10 g.

68. A method according to claim 56, wherein the thyroid hormone is triiodothyronine.

69. A method according to claim 68, wherein the therapeutically effective amount of triiodothyronine is in the range of 50 μg to 1 mg.

* * * * *

UNITED STATES PATENT AND TRADEMARK OFFICE
CERTIFICATE OF CORRECTION

PATENT NO. : 5,158,978
DATED : October 27, 1992
INVENTOR(S) : Leo Rubin

It is certified that error appears in the above-identified patent and that said Letters Patent is hereby corrected as shown below:

```
Title page:   Item 56, 19th line, "infection" should read
-- infarction --.  Col. 6, line 42, "super a ventricular"
should read -- supraventricular --.  Col. 9, line 11,
"claim 42" should read -- claim 52 --.
```

Signed and Sealed this

Thirtieth Day of November, 1993

Attest:

BRUCE LEHMAN

Attesting Officer

Commissioner of Patents and Trademarks